(12) United States Patent
Malak

(10) Patent No.: US 7,704,754 B2
(45) Date of Patent: *Apr. 27, 2010

(54) METHOD OF PLASMON-ENHANCED PROPERTIES OF MATERIALS AND APPLICATIONS THEREOF

(75) Inventor: Henryk Malak, Ellicott City, MD (US)

(73) Assignee: American Environmental Systems, Inc., Ellicott City, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/930,608

(22) Filed: Sep. 1, 2004

(65) Prior Publication Data

US 2005/0164169 A1      Jul. 28, 2005

Related U.S. Application Data

(60) Provisional application No. 60/559,059, filed on Apr. 5, 2004, provisional application No. 60/551,389, filed on Mar. 10, 2004, provisional application No. 60/539,192, filed on Jan. 27, 2004.

(51) Int. Cl.
*G01N 33/551* (2006.01)
(52) U.S. Cl. ...................... 436/524; 436/525
(58) Field of Classification Search ............. None
See application file for complete search history.

(56) References Cited

U.S. PATENT DOCUMENTS

2003/0174384 A1* 9/2003 Halas et al. ............ 359/296

OTHER PUBLICATIONS

Homola et al, "Surface Plasmon Resonance Sensors: Review", Sensors and Actuators B 54 (1999), pp. 3-15.*

* cited by examiner

*Primary Examiner*—Christopher L Chin

(57) ABSTRACT

Methods and applications of surface plasmon resonance-enhanced antibacterial, anti-adhere, adhere, catalytic, hydrophilic, hydrophobic, spectral change, biological and chemical decomposition properties of materials with embedded nanoparticles are disclosed. A method of the nonlinear generation of surface plasmon resonance enables the use of light with wavelengths from X-Ray to IR to enhance properties of materials by several orders of magnitude. The nanoparticle size is crucial for the enhancement and their size is considered to be in the proposed methods and applications within a range of 0.1 nm to 200,000 nm. The nanoparticles preferably are made of noble metals and/or semiconductor oxides. The invention describes a very broad spectrum of applications of surface plasmon resonance-enhanced properties of materials with embedded nanoparticles, from environmental cleanup by road pavement and construction materials, self-cleaning processes of surface materials, thermochromic effects on heat blocking materials, corrosion preventing paint, to sanitization by antibacterial textile fabrics, filters, personal clothing, contact lenses and medical devices.

14 Claims, 6 Drawing Sheets

METHOD OF PLASMON-ENHANCED PROPERTIES OF MATERIALS AND APPLICATIONS THEREOF

CROSS REFERENCE TO RELATED APPLICATIONS

Figure 1:
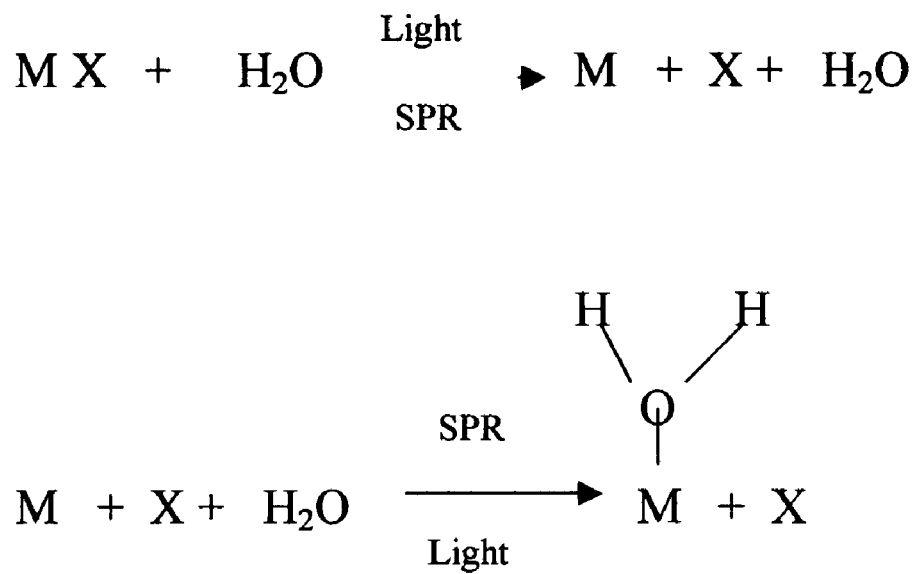

This application is related to U.S. Provisional Patent Application Ser. No. 60/539,192 entitled "Plasmon Enhanced Antibacterial Materials and They Use" filed Jan. 27, 2004, U.S. Provisional Patent Application No. 60/551,389 entitled "Medical Devices Having Plasmon Enhanced Diagnostics, Biomolecule Antiadhere and Antibacterial Materials Thereon" filed Mar. 10, 2004, and to U.S. Provisional Patent Application No. 60/559,059 entitled "Photocatalytic and Hydrophilic Properties of Materials Induced by Surface Plasmons and Application Thereof." filed Apr. 5, 2004 which are herein incorporated by reference.

STATEMENT REGARDING FEDERALLY SPONSORED RESEARCH

There is NO claim for federal support in research or development of this product.

FIELD OF THE INVENTION

The herein disclosed invention finds applicability of nanotechnology in the field of environmental cleanup, sanitization and quality of human health.

BACKGROUND OF THE INVENTION

Photoinduced properties of materials embedded with semiconductor oxides were reported in several patents and papers (U.S. Pat. Nos. 6,194,346, 6,074,981, 6,455,465, 6,524,664, Mor, et al., "A room-temperature TiO2-nanotube hydrogen sensor able to self-clean photoactively from environmental contamination", J. Mater. Res., Vol. 19, No. 2, (2004), Benedix, et al., "Application of Titanium Dioxide Photocatalysis to Create Self-Cleaning Building Materials", Lacer, No.5, (2000), Paz, et al., "Photooxidative self-cleaning transparent titanium dioxide films on glass", J. Mater. Res., Vol. 10, No. 11, p. 2842, (1996)). All of these methods and results presented in patents and papers are based on the ultraviolet light photodecomposition of the semiconductor oxides deposited on the material surfaces that change the physical and chemical properties of these materials. These patents and papers do not teach how to use other wavelengths than UV light and how to use surface plasmon resonance-enhanced effects, nanotechnology advances, and other compounds like noble metals to enhance properties of materials. There were also successful attempts of blue light catalytic effects of semiconductor oxides deposited on material surfaces induced (U.S. Pat. Nos. 6,139,803, 5,874,701). In that case, the semiconductor oxides were embedded to materials which they change the semiconductor oxides ultraviolet light absorption band to the blue light band. However, these materials display substantially reduced photocatalytic properties that limit them to be used in many applications. Again, these inventions do not teach how to use surface plasmon resonance-enhanced effects, nanotechnology advances, and other compounds like noble metals to enhance properties of materials.

Researchers from Hanyang University, South Korea incorporate nano-sized silver particles into polypropylene to produce an anti-microbial material that could be used in anything from carpets, to napkins and surgical masks. Silver has been medically proven to kill over 650 disease-causing organisms in the body and is also very safe. By combining silver and polypropylene to produce an organic-inorganic fiber, researchers have produced the first safe, anti-microbial fiber with a wide range of possible applications. The researchers used nano-sized silver particles to maximizing the surface area and give the optimum antibacterial effect. They found that the fibers containing silver in the core part had no anti-microbial activity and the fibers that included silver in the sheath part showed excellent antibacterial effect. However, this research does not show how to use surface plasmon resonance or other types of energy to significantly enhance antibacterial of textile fabrics, how to induce anti-microbial properties of fiber with embedded metal nanoparticles under fiber surface.

There are a few inventions related to antibacterial materials in which silver is embedded to these material fibers (U.S. Pat. Nos. 6,584,668, 6,087,549, 5,985,301, 5,876,489, 4,340,043). However, in these patents there is no mention of enhancing antibacterial properties of materials induced by plasmon resonance or other types of energy, how to use metals other then silver or metal oxides with antibacterial properties of fabrics, what crucial role play the size and shape of embedded metal nanoparticles to fabrics on antibacterial properties of these fabrics.

There is also great need for "smart materials", e.g. materials whose properties would be altered upon changes of physical parameters of environment surrounding these materials (T. Manning and I. Parkin, "Atmospheric pressure chemical vapour deposition of tungsten doped vanadium(IV) oxide from $VOCl_3$, water and $WCl_6$", J. Mater. Chem., 2554-2559 (2004), U. Qureshi et al., "Atmospheric pressure chemical vapour deposition of $VO_2$ and $VO_2/TiO_2$ films from the reaction of $VOCl_3$, $TiCl_4$ and water",J. Mater. Chem., 1190-1194, (2004)). Currently, there is a very modem success of applying the method of surface plasmon resonance to "smart materials" (Y. Sun and Y. Xia, "Increased Sensitivity of Surface Plasmon Resonance of Gold Nanoshells Compared to That of Gold Solid Colloids in Response to Environmental Changes", Anal. Chem., 74,5297-5305 (2002); Cao, Y.; Jin, R.; Mirkin, C. A. J. Am. Chem. Soc., 123, 7961 (2001)). The observed, in these reports, surface plasmon resonance-enhanced spectral changes upon changing environment of surrounding materials are within 50 nm. In this method, the environmentally sensitive polymer covering metal nanoparticles alters its own properties upon changes in the environment, which leads to spectral changes of a SPR absorption band. These modest spectral changes are good enough to built biochemical sensors, but not sufficient to apply them in "smart materials", where drastic spectral changes would be desired. For example, there is great need to observe spectral changes by a few hundreds nanometers in glass windows upon sunlight heat, which can cause blocking infrared sunlight by glass window when temperature of the glass is to high. Hence, there is great need for new methods which significantly would change properties of materials. The disclosed below invention shows a novel methodology how to enhance properties of materials by many orders of magnitude, to overcome limitations of conventional methods and provides novel applications of surface plasmon resonance-enhanced photocatalytic and other properties of materials.

SUMMARY DESCRIPTION OF THE PATENT

Methods and applications of surface plasmon resonance-enhanced photocatalytic, hydrophilic/hydrophobic, antibacterial, anti-microbial, anti-adhering/adhering, spectral change, biological and chemical decomposition properties of materials with the embedded nanoparticles are disclosed in a present invention. In the embedded nanoparticles, under excitation of electromagnetic radiation and/or under other forms of energy, are generated extremely strong surface plasmon resonance electromagnetic fields, ultrasound, heat and other types of energy, which interact with the nearby chemical and biological molecules and with the material. The enhancement of these interactions is from hundreds to millions times and more. The nonlinear generation of surface plasmon resonance combined with nonlinear optical excitation enable the use of a broad spectrum of light within a range of 0.001 nm to 20,000 nm in the proposed methods and applications. The embedded nanoparticle sizes are crucial to the proposed surface plasmon resonance enhancements and their sizes are considered to be within a range of 0.1 nm to 200,000 nm. In the present invention the use of the embedded nanoparticles made of noble metals and/or semiconductor oxides is also preferable, in which the enhancement effects are very evident and mechanism of the interactions with surrounding molecules and the material is less difficult to explain. There is very broad spectrum of applications for the proposed methods in the present invention, from environmental cleanup by embedding the nanoparticles to road pavement materials or construction materials, to antibacterial properties of textile fabrics, filters, personal clothing, contact lenses, and medical devices.

FIGURES DESCRIPTION

FIG. 1. shows photocatalytic reactions of a metal oxide molecule (MX) and water molecule in the presence of light. Light breaks the metal oxide molecule (MX) to a metal (M) and non-metal species. The metal (M) under light absorption generates surface plasmon resonance (SPR) and interacts with nearby environment attracting electron unsaturated molecules like water. The non-metal species interact with nearby molecules.

Figure 2:
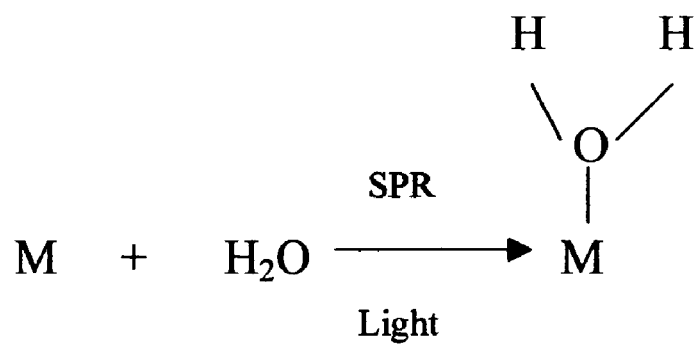

FIG. 2. shows a photocatalytic reactions of a metal (M) and water molecule in the presence of light. The metal under light absorption generates surface plasmon resonance (SPR) and interacts with nearby environment attracting electron unsaturated molecules like water.

Figure 3:
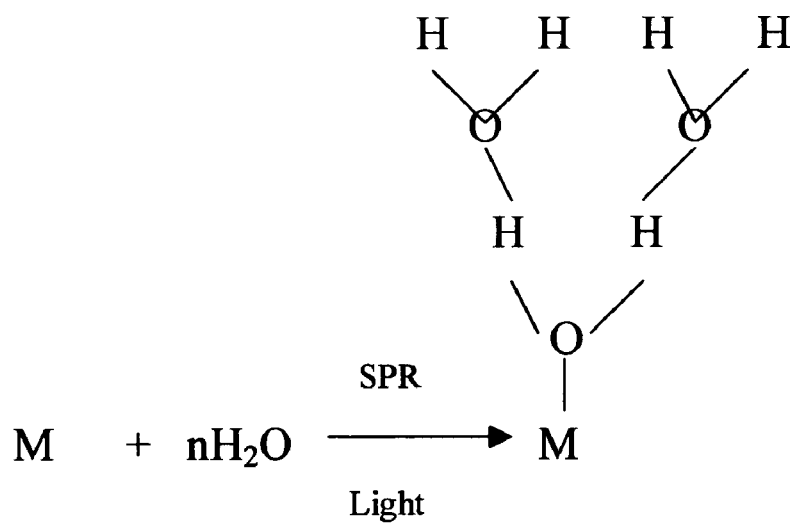

FIG. 3. shows a surface plasmon resonance (SPR)-induced hydrophilicity of a metal (M) in the presence of water molecules and light. The metal under light absorption generates SPR and interacts with nearby environment attracting electron unsaturated molecules like water.

Figure 4:
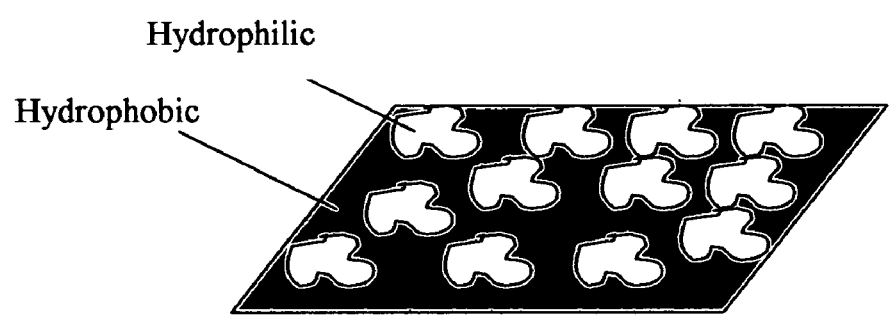

FIG. 4. illustrates areas of a surface plasmon resonance (SPR)-induced hydrophilicity and hydrophobicity of a material.

Figure 5:
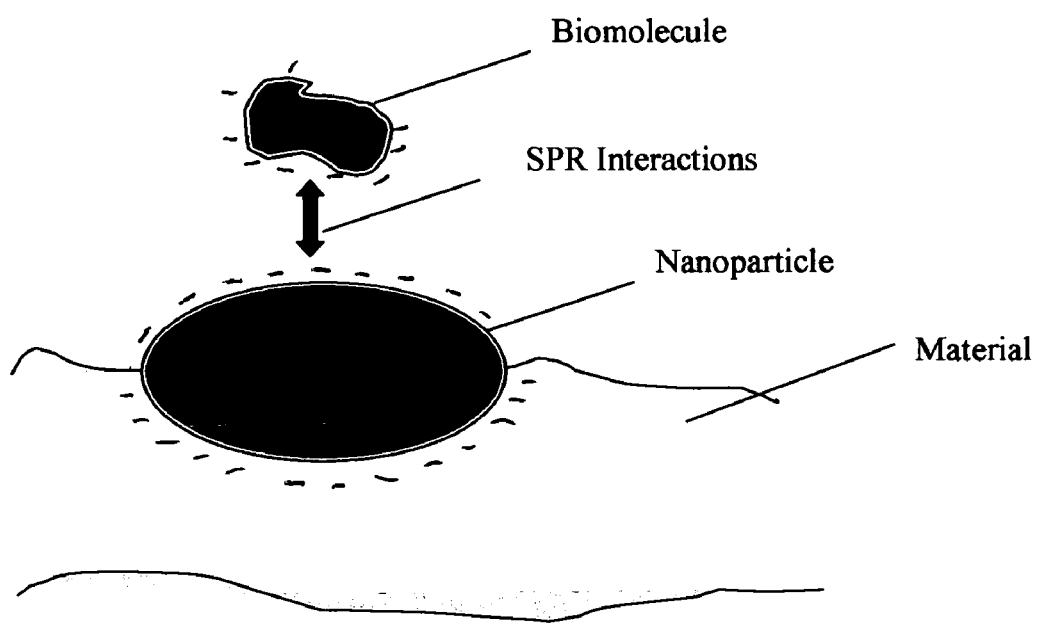

FIG. 5. illustrates a surface plasmon resonance (SPR)-induced anti-adhering properties of a material. The nanoparticle excited by SPR is negatively charged and repel negatively charged biomolecule.

Figure 6:
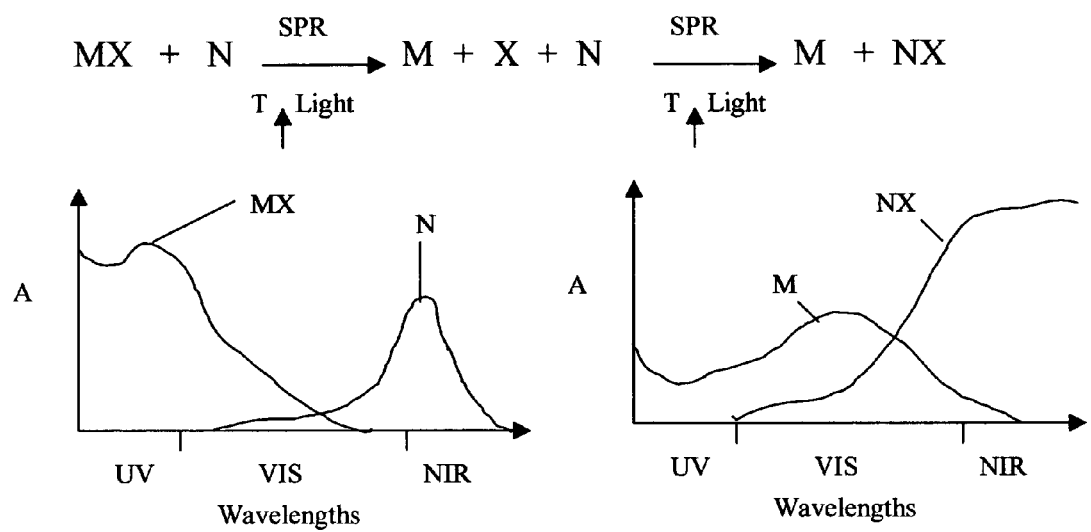

FIG. 6. shows a thermochromic dissociation reaction of a metal complex (MX) under SPR absorption of another metal (N) and/or the metal complex and higher temperature, and a thermochromic redissociation of a non-metal ligand (X) with the metal (N) under higher temperature. The bottom part of this figure shows absorption spectra of chemical components in these SPR-induced thermochromic reactions.

Figure 7:
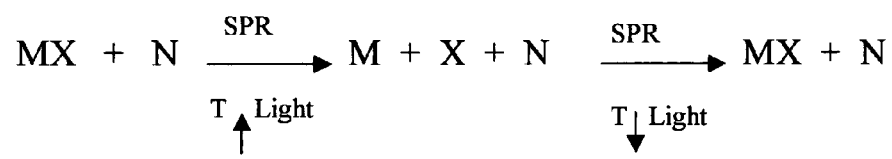
Figure 7:
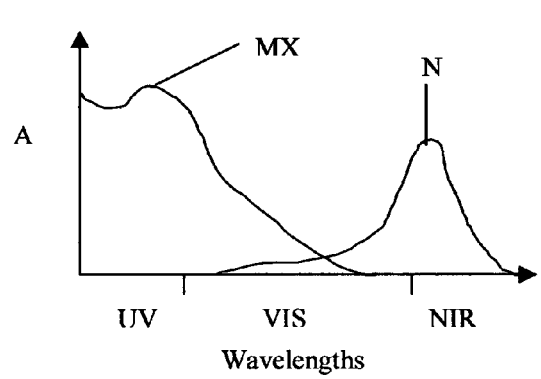
Figure 7:
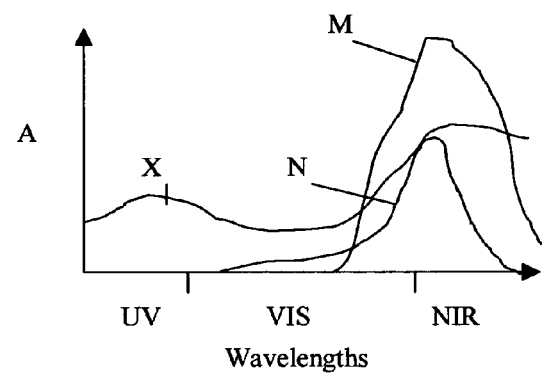

FIG. 7. shows a thermochromic dissociation reaction of a metal complex (MX) under SPR absorption of another metal (N) and/or the metal complex and higher temperature, and a thermochromic redissociation of a non-metal ligand (X) with a metal (M) under SPR absorption and lower temperature. The bottom part of this figure shows absorption spectra of chemical components in these SPR-induced thermochromic reactions.

Figure 8:
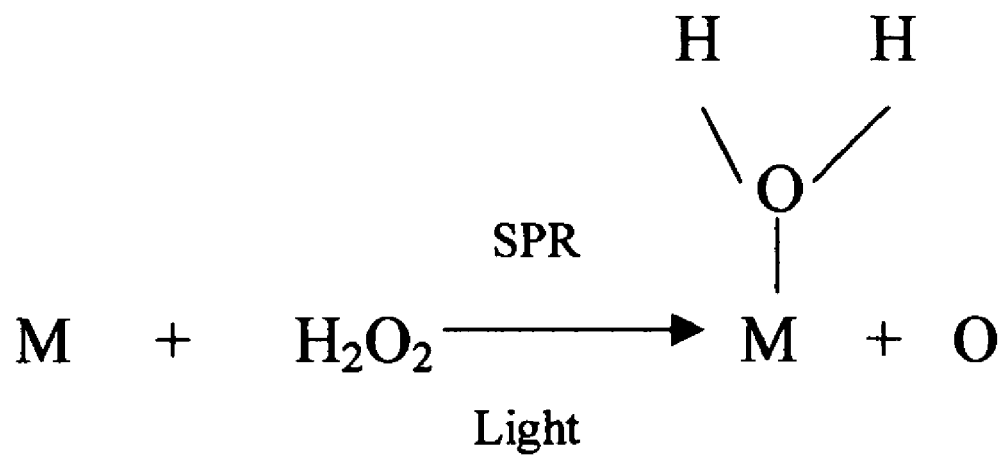

FIG. 8. shows one of many examples of a chemical enhancement of SPR-enhanced properties of materials. Hydrogen peroxide interacts with metal nanoparticles (M) in the presence of SPR and light. The hydrogen peroxide molecules will decompose to water molecules which under SPR will make complexes with the metal nanoparticles (M) and the released atomic oxygen molecules will very aggressively oxidize nearby molecules. Hence, the hydrophilicity and highly oxygenation properties of material will be created.

DETAIL DESCRIPTION OF THE INVENTION

1. Abbreviations and Definitions

CW optical source—continuous waves source

SPR-surface plasmon resonance generated in a nanoparticle under illumination by electromagnetic radiation and other forms of energy one-photon mode of excitation—process in which molecule is excited by a one photon absorption event two-photon mode of excitation—process in which molecule is excited by simultaneous absorption of two photons multi-photon mode of excitation—process in which molecule is excited by simultaneous absorption of three or more photons step-wise mode of excitation—process in which molecule is excited by absorption of one photon and subsequently by absorption of second photon up-conversion mode of excitation—process in which a molecule is excited by lower energy photon than energy of the lowest excited state of the molecule metal island—a nanoparticle on a substrate without defined shape thermochromic reaction—a reaction which undergoes a temperature change and is associated with a spectral change.

2. Exemplary Embodiments

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates to a novel method of plasmon-induced catalytic properties of materials. In the proposed method, a nanoparticle capable of inducing a catalytic property in the material is embedded into a material, and then the nanoparticle is excited by radiation from a plasmon source that causes generation of plasmon fields in the excited nanoparticle which they interact with the material and induce a catalytic property in the material. Because, the intensities of the plasmon fields are surface dependent of the excited nanoparticle and square dependent of intensity of the plasmon source, the induced catalytic effect in the material can be very pronounced and can be used in various applications stated in the embodiments of this invention. The plasmon-induced catalytic property of the material can be hydrophilic, hydrophobic, antibacterial, anti-adhere, or adhere, The type of the plasmon-induced property of the material can be controlled by the material or by the nanoparticle, as it is disclosed in this invention. The location of the plasmon induced catalytic property in the material can be spatially controlled by the nanoparticle and/or by localized excitation of the plasmon source.

The present invention expands the above scientific findings to new methods and new applications of the SPR-enhanced interactions of nanoparticles embedded into a material with the nearby biological and chemical substances and with the material. The SPR excited nanoparticles interact extremely strong with the substances that are in direct contact with them. In the contact, SPR-enhanced interactions usually lead to decomposition of these substances. In the direct contact interactions, the nanoparticles play mostly a catalytic role. The SPR excited nanoparticles also interact with nearby molecules which are not in direct contact with them. At nearby distances from the SPR excited nanoparticles exist very intense SPR electromagnetic fields (plasmons) (Ditlbacher H. et al., *Appl. Phys.* B 73, 373-377 (2001)), thermal energy due to SPR absorption by the nanoparticles (Hirsch et al., *PNAS*, 100, 13549-13554 (2003)), ultrasound (S. Coyle, et al., *Phys. Rev. Let.* 87(17), 176801, (2001)) and other types of SPR generated energy. The SPR-enhanced interactions between the nanoparticles and nearby surrounding molecules can be million times or much higher than these interactions without SPR. Practically, without SPR, the only significant interactions of nanoparticles with other substances occur when they are in direct contact, but the strength of these interactions is many orders of magnitude weaker than in the presence of SPR. Therefore, prior art research findings indicate that for example antibacterial properties of materials exist only when metal particles are in direct contact with bacteria.

The enormous SPR-enhanced interactions of the nanoparticles with nearby or in contact biological and chemical substances can be applied very effectively to environmental cleanup, corrosion protective technology, sanitization and other applications, which will have positive impact on human health and economics.

The SPR-enhanced interactions of the nanoparticles with surrounding molecules are mainly catalytic interactions when nanoparticles are selected from the group of metals, metal oxides and semiconductors. Examples of catalytic reactions are shown on FIG. 1 and FIG. 2. When the energy of light is sufficient to breakdown a metal complex (MX) (e.g. like it is in titanium dioxide, the UV light separates oxygen species from titanium), a metal (M) becomes the SPR source of electromagnetic fields, ultrasound, heat and other forms of energy that induced new properties of materials, and non-metal species (X) aggressively interact with nearby biological and chemical substances. The SPR induced electromagnetic fields are very intense and electric field strength can be as high as $\sim 10_7$ V/m that can cause breakdown in condensed materials including nearby biological and chemical substances (N. Bloembergen, "Laser-induced electric breakdown in solid", *IEEE. J. Quan. Electron.*, 10, pp.375-386 (1974); D. Stern, R. W. Schoenlein, C. A. Puliafito, E. T. Dobi R. Biringruber, J. G. Fujimoto, "Corneal ablation by naonosecond, picosecond, and femtosecond lasers at 532 and 625 nm", *Arch. Ophthalrnol.*, 107,587-592 (1989)). The breakdown in condensed materials mainly is related to the separation of electric charges in the material area located nearby the SPR excited nanoparticle. The separation of electric charges induces new properties in the material like hydrophilicity/hydrophobicity (FIG. 3 and FIG. 4) and/or anti-adhering/adhering properties (FIG. 5). The SPR induced hydrophilicity may remain for a long time (minutes, hours) in dielectric or semiconductor type materials. The SPR induced hydrophilicity in the material leads also to increasing hydrophobicity in the other areas of this material (FIG. 4.). Therefore, the proposed in the invention method of the SPR induced hydrophilicity and hydrophobicity can be applied for very efficient cleaning of dielectric and semiconducting materials like glass, porcelain, silicon, silicon dioxide, plastic, textile natural and synthetic fibers, but not limited only to them. The hydrophilicity and hydrophobicity properties of the material allows for easy cleaning of inorganic and organic substances from the surface of this material. e.g. organic substances can be very easily cleaned by inorganic substances and inorganic substances can be very easily cleaned by organic substances. The area of the SPR-enhanced hydrophilicity and hydrophobicity and the other SPR enhanced properties of material depend on the electric field strength of the SPR electromagnetic fields. As was demonstrated by Ditlbacher (Ditlbacher, H. et al., *Appl. Phys.* B 73, 373-377 (2001)), SPR electromagnetic fields can exist at distance of 10 microns from the SPR excited nanoparticles. Therefore, the area of SPR enhanced hydrophilicity and hydrophobicity and other SPR enhanced properties of material can be as large as 100 square microns or more. The smallest area is limited by the nanoparticle size, and can be as small as a few square nanometers.

Another embodiment of the present invention is a method of the SPR-enhanced anti-adhering and/or adhering properties of materials. The SPR-enhanced anti-adhering properties of materials depend on separation of charges in the embedded nanoparticles under SPR absorption, strength of SPR electromagnetic fields, amount of heat and other types of energy released by the nanoparticle after SPR absorption and also depend on electronic structure and other properties of material. For example, the metal nanoparticle became very negatively charge after SPR absorption and it will repel any nearby molecules with a negative charge (FIG. 5). Therefore, most biological negatively charged substances would have difficulty to adhere to material surfaces with embedded metal nanoparticles. This SPR anti-adhering property of the materials is proposed in this invention to apply to contact lenses and surfaces of medical instruments (but not limited to them). The negatively charged SPR excited metal nanoparticles have also adhering properties for molecules with positive charge. The SPR controlled adhesivity of materials may have many applications and they are also a part of the present invention. One of many scenarios of the SPR controlled anti-adhering and adhering properties of the materials could be an application, in which UV light is used for the SPR-enhanced adhering properties of the material, and red light is used for the SPR-enhanced anti-adhering properties of this material. For example, the UV light induced adhering properties of the material can be related to the SPR electromagnetic fields-enhanced interaction with energy of the electronic structures of the material molecules which leads to stiffening chemical bonds in the material and the red light induced anti-adhering properties of this material can be related to generated heat or other forms of energy by SPR absorbed nanoparticles.

The SPR enhanced anti-adhering contact lenses materials may also have SPR-enhanced antibacterial properties. Both of these SPR-enhanced properties of contact lenses described in the present invention may change quality of life for many people wearing them. Additionally, a color of the contact lenses can be selected by designing a size, shape and coat of embedded nanoparticles.

Anyone of ordinary skill in the art will appreciate that the present invention considers nonlinear generation of SPR to enhance antibacterial, anti-adhere/adhere, catalytic, hydrophilic/hydrophobic, spectral change, and biological and chemical decomposition properties of materials. The nonlinear generation of SPR by one-photon excitation can be expanded to nonlinear optical generation of SPR by two-photon, multi-photon, step-wise photons and up-conversion. It means that SPR generated in embedded nanoparticles by blue, visible and Near Infrared light may enhance properties of materials in a similar way, as does UV light. Therefore, our invention is not restricted to the specific wavelengths, and we propose to use light wavelengths for nonlinear SPR generation within the range of 0.001 nm to 20,000 nm. The optical nonlinearity provides also the capability of three-dimensional localized SPR-enhanced properties of the material with a spatial resolution at diffraction limit. The method of the three-dimensionally SPR controlled properties of materials may find many applications like controlling externally chemical reactions in materials, using hydrophilicity versus hydrophobicity to change material structure, providing adhering control in materials, making a three-dimensional memory material, but the method is not limited to these applications.

The SPR-enhanced antibacterial and anti-adhering properties of the materials can be also applied to textile fabrics like personal clothing, filters, carpets, door mats, but not limited to them. The nanoparticles can be embedded to natural or synthetic textile fabrics by woven process, spraying colloidal nanoparticles on the fabrics, soaking fabrics in colloidal solution or by other methods. Some type of nanoparticles embedded in personal clothing may stain the clothing, and therefore these nanoparticles should be coated with a stain preventing material. Usually, discolorations by nanoparticles are related to oxidation processes, and to inhibit these processes it is advisable to cover nanoparticles with a thin film of a protective material. The protective material may also help to optimize the best SPR-enhanced antimicrobial properties of materials.

Another embodiment in the present invention is a method of SPR-enhanced spectral changes in materials upon physical and biochemical changes of the environment surrounding these materials. In the method, spectral changes of materials with embedded nanoparticles are induced and controlled by SPR and light. An example of the method applied to thermochromic properties of materials is described here in the two scenarios. In scenario # 1, a material is embedded with a nanoparticle composite of a metal complex (MX) and another doped metal (N). Preferably the other metal (N) has an oxidation number higher than the oxidation number of a metal (M) in the metal complex (MX). Under SPR absorption by the metal complexes (MX) and/or by the other metal (N), the metal complex (MX) remains as the complex as long as the temperature of the nanoparticle is not high enough to break the complex. Above a certain temperature of the nanoparticle composite the complex dissociates, and a non-metal ligand in the complex (X) is attracted by another metal (N) in the nanoparticle composite and forms a new complex (NX) with very different spectral properties (FIG. 6). In scenario # 2, the same nanoparticle composite as in the scenario # 1 generates heat upon SPR absorption that breaks the complex (MX) and the metal (M) and non-metal ligand (M) have different spectral properties. In the scenario # 2, redissociation process occurs when the temperature of the material nanoparticle decreases (FIG. 7). In scenarios # 1 and # 2, the contribution of SPR electromagnetic fields and other forms of energy generated by SPR are also considered a part of this invention.

Another embodiment in the present invention is a method of an additional enhancement of SPR-enhanced properties of material by the presence of a chemical substance, biological substance and/or drug. One of many examples of this embodiment can be the use of hydrogen peroxide on a material surface coated with metal nanoparticles (M) (FIG. 8). In the presence of SPR and light the hydrogen peroxide molecules will decompose to water molecules that under SPR will make complexes with the metal nanoparticles (M) creating hydrophilic properties of the material and the released atomic oxygen molecules will very aggressively oxidize nearby molecules.

Anyone of ordinary skill in the art will appreciate that the present invention applies also to corrosion protective paints. The SPR-enhanced properties of materials and/or the presence of chemical and/or biological substances can be used to absorb and neutralize corrosion causing substances. In this method, one of many scenarios is as follow. The nanoparticles embedded to a corrosion protective paint, under SPR-enhanced photocatalytic reactions with or without chemical additives, decompose corrosion causing substances. The photocatalytic reactions can be controlled by amount of nanoparticles and/or by chemical additives in the corrosion protective paint. In the paint, nanoparticles and chemical additives can also be covered by environmentally sensitive polymer that upon environmental conditions will release a desired amount of the nanoparticles and chemical additives into the paints to decompose corrosion causing substances. This polymer may also release nanoparticles at a specific rate into the paint in spite of environmental conditions. The paint may also provide indication about the progress of corrosion on material surfaces by developing spectral signatures upon SPR-enhanced photocatalytic reactions of nanoparticles with the corrosion substances and/or with corroded substances on material surfaces. The spectral signatures of the corrosion progress can be measured visually or by instrument. The presented method can be applied to metal type surfaces and as well to dielectric, semiconductor and other type surfaces.

Another embodiment of the present invention is a method of using surface plasmon resonance-enhanced properties of a material surface in a device for diagnostics purposes. The method also includes the enhancement of fluorescence and Raman signal. Biological substances considered in this invention are selected from the group of a biomolecule, bacteria, protein, tissue, skin, cells, body fluid, bacteria, virus, pathogen, biochemical warfare agent (but not limited to them).

Chemical substances considered in this invention are selected from the group of an inorganic molecule, organic molecule, mixture of inorganic and organic molecules, drug, chemical warfare agent (but not limited to them).

Medical devices considered in the invention are catheters, colonscopes, endoscopes, and any medical devices which are in contact with human or animal body. Embedded nanoparticles considered in this invention are: metal, metallic composite, metal oxide, metallic salt, electric conductor, electric superconductor, electric semiconductor, dielectric, quantum dot, metal-dielectric composite, metal-semiconductor composite, metal-semiconductor-dielectric composite (but not limited to them). The invention considers the use for generation of SPR in the embedded nanoparticles electromagnetic radiation sources such as CW/pulsed and polarized/non-polarized light sources like lamps, LEDs, single and/or multi-wavelength lasers for the SPR enhanced properties of the materials. However, SPR can also be generated by other techniques like sonic waves or electrical technologies, electrostatic, ultrasound, magnetic technologies. Therefore, these other techniques of generation SPR are also considered as a part of the present invention, particularly if these techniques are combined with optical techniques.

What is claimed is:

1. A method of creating surface plasmon induced properties in materials comprising steps of: providing a material; providing a nanoparticle capable of creating a surface plasmon induced property in the material by interactions of surface plasmon electric fields of the excited nanoparticle with the material; providing a surface plasmon source; embedding the nanoparticle into the material by mixing the nanoparticle with the material or by allowing the nanoparticle to be adsorbed by the material; and exciting the embedded nanoparticle by the surface plasmon source.

2. The method of claim 1, wherein the nanoparticle is metal, metal oxide, metal dioxide, metallic salt, intermetallic alloy, transition metal, quantum dot, electric conductor, electric superconductor, electric semiconductor, or semiconductor doped with metal.

3. The method of claim 2, wherein metal is selected from the group consisting of: silver, silver oxide, silver ion, silver nitrate, ruthenium, platinum, palladium, cobalt, rhenium, rhodium, osmium, iridium, copper, aluminum, aluminum oxide, aluminum alloy, zinc, zinc oxide, nickel, chromium, magnesium, magnesium oxide, tungsten, iron, palladium, gold, titanium, titanium oxide, titanium dioxide, titania, alkaline earth metal, selenium, cadmium, vanadium, vanadium oxide, or molybdenum.

4. The method of claim 1, wherein the nanoparticle has a size within a range of 0.1 nm to 200,000 nm in at least one of its dimensions.

5. The method of claim 4, wherein the nanoparticle is a thin film, colloid, fiber, metal island, nanowire, nanotube, empty shell, shell filled with a conducting material, or shell filled with a dielectric material.

6. The method of claim 1, wherein the nanoparticle is a non-coated nanoparticle, or a coated nanoparticle.

7. The method of claim 6, wherein the coated nanoparticle is coated by a semiconductor, conductor, biochemical substance, polymer, light sensitive polymer, disintegrating in time polymer, or environmentally sensitive polymer.

8. The method of claim 7, wherein said coating material of said embedded nanoparticle has thickness within a range of 1 nm to 200,000 nm.

9. The method of claim 1, wherein the material is a dielectric, conductor, semiconductor, silicon oxide, zeolite, mesoporous material, construction material, paint material, road pavement material, glass, ceramic, plastics, silicone, silica, adhesive material, corrosion protective material, packaging material, contact lenses material, optical material, thermochromic material, quartz, polymer, polypropylene, aqueous solution, organic solution, air, gas, textile fabric, cellulose based material, or biological material.

10. The method of claim 1, wherein the plasmon source is a single energy source or a multiple energy source selected from the group consisting of: electromagnetic, ultrasound, thermal, electric, electrostatic, magnetic, ionizing radiation, or mechanical.

11. The method of claim 10, wherein the electromagnetic radiation source is selected from the group consisting of: a laser with single wavelength, laser with plurality wavelengths, semiconductor laser, pulsed laser, Q-switched laser, light emitted diode, lamp, bioluminescence, sunlight, fluorescence, chemiluminescence, electroluminescence, luminescence, and X-Rays.

12. The method of claim 1, wherein the plasmon induced property of the material is selected from the group of: hydrophilic, hydrophobic, antibacterial, anti-adhere, adhere, or chemically reactive.

13. The method of claim 1, wherein the plasmon induced property of the material is spatially controlled in the material by the plasmon source or by location of the nanoparticle in the material.

14. The method of claim 1, wherein the plasmon induced property of the material is controlled by the nanoparticle or the material.

* * * * *